(12) United States Patent
Kennedy

(10) Patent No.: US 11,337,905 B2
(45) Date of Patent: May 24, 2022

(54) ANTI-AGING AND SKIN TONE LIGHTENING COMPOSITIONS AND METHODS FOR SAME

(71) Applicant: Truetiva Inc., Grand Rapids, MI (US)

(72) Inventor: J. Phillip Kennedy, Grand Rapids, MI (US)

(73) Assignee: Truetiva, Inc., Grand Rapids, MI (US)

( * ) Notice: Subject to any disclaimer, the term of this patent is extended or adjusted under 35 U.S.C. 154(b) by 0 days.

(21) Appl. No.: 16/246,823

(22) Filed: Jan. 14, 2019

(65) Prior Publication Data

US 2019/0216695 A1 Jul. 18, 2019

Related U.S. Application Data

(60) Provisional application No. 62/617,215, filed on Jan. 13, 2018, provisional application No. 62/702,973, filed on Jul. 25, 2018.

(51) Int. Cl.
*A61K 8/34* (2006.01)
*A61K 8/06* (2006.01)
*A61Q 19/02* (2006.01)
*A61Q 19/08* (2006.01)

(52) U.S. Cl.
CPC ............... *A61K 8/34* (2013.01); *A61K 8/062* (2013.01); *A61K 8/064* (2013.01); *A61K 8/347* (2013.01); *A61Q 19/02* (2013.01); *A61Q 19/08* (2013.01)

(58) Field of Classification Search
None
See application file for complete search history.

(56) References Cited

U.S. PATENT DOCUMENTS

| 2014/0271940 A1* | 9/2014 | Wurzer .................. A61P 25/00 424/725 |
| 2015/0086494 A1* | 3/2015 | Sekura .................. A61K 36/00 424/59 |
| 2015/0245991 A1* | 9/2015 | Nihart ...................... A61K 8/97 424/728 |
| 2016/0235661 A1* | 8/2016 | Changoer ............ A61K 9/0014 |

FOREIGN PATENT DOCUMENTS

| CN | 107982080 A | * | 5/2018 | ............... A61K 8/34 |
| KR | 1020130125493 A | * | 11/2013 | ........... A61K 36/185 |

OTHER PUBLICATIONS

Google Translation of CN107982080A (Year: 2018).*

* cited by examiner

*Primary Examiner* — Kyung S Chang
(74) *Attorney, Agent, or Firm* — Frost Brown Todd LLC

(57) ABSTRACT

Embodiments of the invention are directed to compositions containing cannabinoid, cannabidiol, or cannabidiol analog for lightening or whitening skin, and methods for lightening skin tone or whitening skin by administering compositions containing cannabinoid, cannabidiol, or cannabidiol analog to the skin.

17 Claims, 4 Drawing Sheets
(4 of 4 Drawing Sheet(s) Filed in Color)

ANTI-AGING AND SKIN TONE LIGHTENING COMPOSITIONS AND METHODS FOR SAME

CROSS-REFERENCE TO RELATED APPLICATIONS

This application claims priority from U.S. Provisional Application No. 62/617,215 entitled "Compositions For Lightening Skin Tone And Methods For Same," filed Jan. 13, 2018 and U.S. Provisional Application No. 62/702,973 entitled "Anti-aging Compositions And Compositions For Lightening Skin Tone And Methods For Same," filed Jul. 25, 2018 the disclosures of which are hereby incorporated by reference in their entireties.

GOVERNMENT INTERESTS

Not applicable

PARTIES TO A JOINT RESEARCH AGREEMENT

Not applicable

INCORPORATION OF MATERIAL ON COMPACT DISC

Not applicable

BACKGROUND

Cannabinoids are a class of diverse chemical compounds that act on cannabinoid receptors on cells that modulate physiological responses in the brain, peripheral nervous and immune systems. The native endocannabinoid ligands (produced naturally in the body by humans and animals), the phytocannabinoids (found in cannabis and some other plants), and synthetic cannabinoids (manufactured chemically) bind to receptors throughout the body and control downstream signal transduction. One example of a cannabinoid is Cannabidiol (CBD), which is a major substituent in hemp and hemp extracts. It may have multiple potential applications such as for the treatment of epilepsy and other motor disorders, inflammation, mood and anxiety disorders, sleep dysfunction and eating disorders. CBD is also considered a promising antineoplastic agent on the basis of its in vitro and in vivo activity against tumor cells.

The endocannabinoid system (ECS) regulates many physiological processes involved in relaxation, eating, sleeping, certain inflammatory responses and even cognitive function. There are two types of cannabinoid receptors found throughout the body (CB1 and CB2), but they are most abundant in the brain and immune system respectively. In fact, the CB1 receptor is the most densely populated G-coupled protein receptor in the human brain. New evidence indicates that a cannabinoid-like ligands act on wide variety of biological targets, such as the transient receptor potential cation channel, nuclear receptors and other orphaned G-coupled protein receptors (i.e., TRPV1, PPAR, GPR18 and GPR55), and represents a fascinating area to develop new therapeutic targets.

SUMMARY OF THE INVENTION

Various embodiments are directed to topical formulations containing a cannabinoid, cannabidiol, or cannabidiol analog, a carrier, excipient, diluent, reagent, or combinations thereof, and an additive. Other embodiments include methods for lightening skin tone including topically administering a composition containing a cannabinoid, cannabidiol, cannabidiol analog, or combinations thereof, where lightening encompasses lightening color of skin, reducing production of melanin, diminishing the amount of melanin in skin, reducing visible redness, or combinations thereof.

Some embodiments are directed to topical anti-aging formulations. The anti-aging formulations may include cannabidiols, cannabidiol isomers, cannabidiol analogs, or combinations thereof and a carrier, excipient, diluent, reagent, or combinations thereof. And in some embodiments, such formulations may further include one or more anti-oxidants, anti-wrinkling agents, anti-inflammatory agents, emollients, proactants, conditioning agents, and combinations thereof. Such formulations may interrupt or prevent the production of tyrosinase and melanin and may a provide a reduction in fine lines and wrinkles as well as firming and lifting of the skin to reduce notable sagging.

DESCRIPTION OF THE DRAWINGS

The patent or application file contains at least one drawing executed in color. Copies of this patent or patent application publication with color drawing(s) will be provided by the office upon request and payment of the necessary fee.

For a fuller understanding of the nature and advantages of the present invention, reference should be made to the following detailed description taken in connection with the accompanying drawings, in which:

FIG. 1A shows right (treated) and left (control) hands of a subject prior to treatment with a CBDA skin lightening composition.

FIG. 1B shows right (treated) and left (control) hands of the subject of FIG. 1A after 14 days of twice daily treatment with a CBDA skin lightening composition.

FIG. 1C shows right (treated) and left (control) hands of the subject of FIG. 1A after 35 days of twice daily treatment with a CBDA skin lightening composition.

Figure 1A:
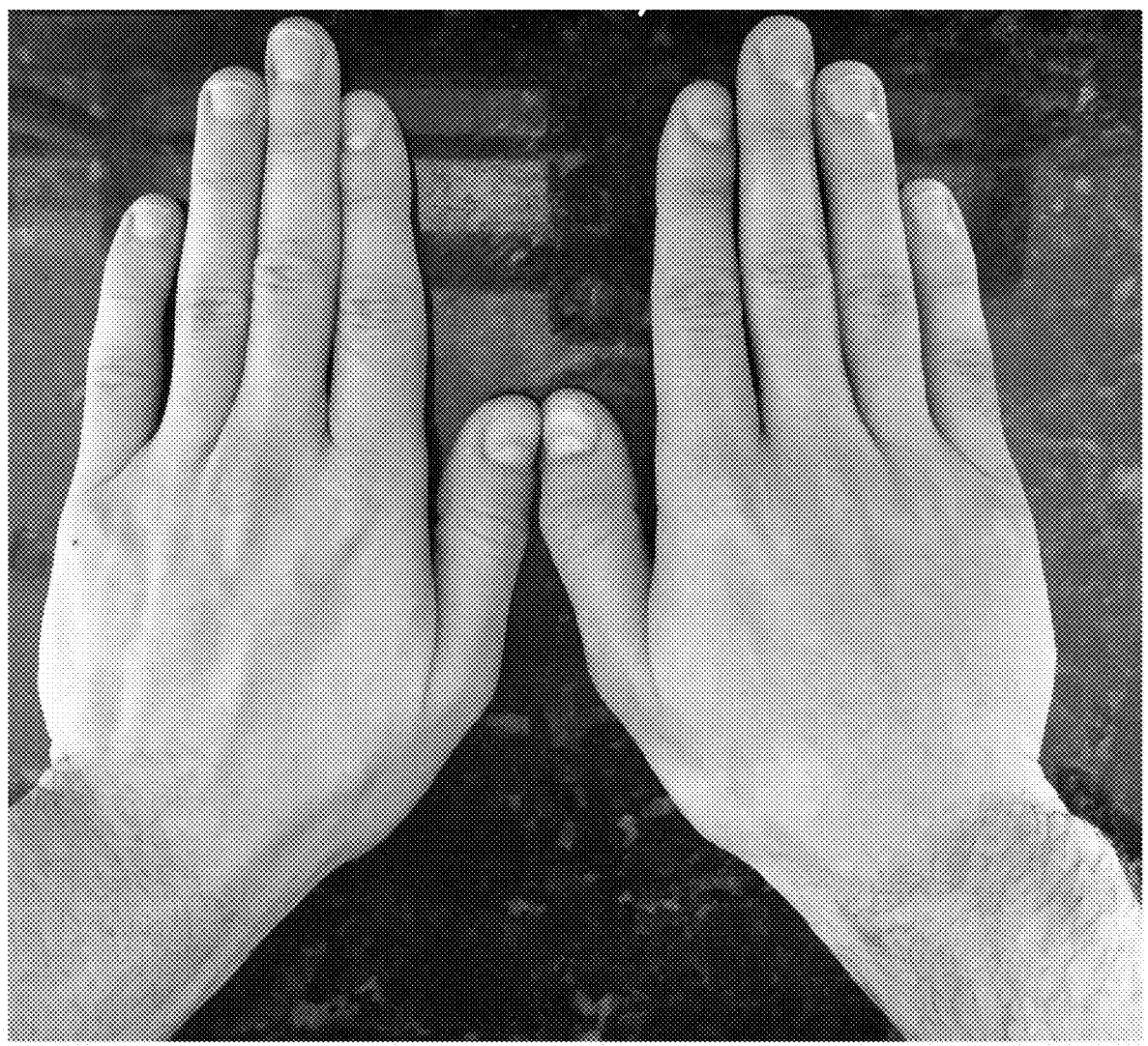
FIG. 1A-C shows the effects of skin exposed to cannabidiol containing fluids that exhibits significantly lighter skin tone, reduction pigmentation, and reduction of observable blemishes, such as, freckles.

The patent or application file contains at least one drawing executed in color. Copies of this patent or patent application publication with color drawing(s) will be provided by the Office upon request and payment of the necessary fee.

DETAILED DESCRIPTION

Where a range of values is provided, it is intended that each intervening value between the upper and lower limit of that range and any other stated or intervening value in that stated range is encompassed within the disclosure. For example, if a range of 1 um to 8 um is stated, 2 um, 3 um, 4 um, 5 um, 6 um, and 7 um are also intended to be explicitly disclosed, as well as the range of values greater than or equal to 1 um and the range of values less than or equal to 8 um.

All percentages, parts and ratios are based upon the total weight of the topical compositions and all measurements made are at about 25° C., unless otherwise specified.

The singular forms "a," "an," and "the" include plural referents unless the context clearly dictates otherwise. Thus, for example, reference to a "polymer" includes a single polymer as well as two or more of the same or different polymers; reference to an "excipient" includes a single excipient as well as two or more of the same or different excipients, and the like.

The word "about" when immediately preceding a numerical value means a range of plus or minus 10% of that value, e.g., "about 50" means 45 to 55, "about 25,000" means 22,500 to 27,500, etc., unless the context of the disclosure indicates otherwise, or is inconsistent with such an interpretation. For example, in a list of numerical values such as "about 49, about 50, about 55, about 50" means a range extending to less than half the interval(s) between the preceding and subsequent values, e.g., more than 49.5 to less than 52.5. Furthermore, the phrases "less than about" a value or "greater than about" a value should be understood in view of the definition of the term "about" provided herein.

The terms "administer," "administering" or "administration" as used herein refer to either directly administering a compound (also referred to as an agent of interest) or pharmaceutically acceptable salt of the compound (agent of interest) or a composition to a subject.

The term "carrier" as used herein encompasses carriers, excipients, and diluents, meaning a material, composition or vehicle, such as a liquid or solid filler, diluent, excipient, solvent or encapsulating material involved in carrying or transporting a pharmaceutical, cosmetic or other agent across a tissue layer such as the stratum corneum or stratum spinosum.

The transitional term "comprising," which is synonymous with "including," "containing," or "characterized by," is inclusive or open-ended and does not exclude additional, unrecited elements or method steps. By contrast, the transitional phrase "consisting of" excludes any element, step, or ingredient not specified in the claim. The transitional phrase "consisting essentially of" limits the scope of a claim to the specified materials or steps "and those that do not materially affect the basic and novel characteristic(s)" of the claimed invention. In embodiments or claims where the term comprising is used as the transition phrase, such embodiments can also be envisioned with replacement of the term "comprising" with the terms "consisting of" or "consisting essentially of."

The phrase "pharmaceutically acceptable" or "cosmetically acceptable" is employed herein to refer to those agents of interest/compounds, salts, compositions, dosage forms, etc, which are—within the scope of sound medical judgment suitable for use in contact with the tissues of human beings and/or other mammals without excessive toxicity, irritation, allergic response, or other problem or complication, commensurate with a reasonable benefit/risk ratio. In some aspects, pharmaceutically acceptable means approved by a regulatory agency of the federal or a state government, or listed in the U.S. Pharmacopeia or other generally recognized pharmacopeia for use in mammals (e.g, animals), and more particularly, in humans.

The term "salts" as used herein embraces pharmaceutically acceptable salts commonly used to form alkali metal salts of free acids and to form addition salts of free bases. The nature of the salt is not critical, provided that it is pharmaceutically acceptable. The term "salts" also includes solvates of addition salts, such as hydrates, as well as polymorphs of addition salts. Suitable pharmaceutically acceptable acid addition salts can be prepared from an inorganic acid or from an organic acid. Non-limiting examples of such inorganic acids are hydrochloric, hydrobromic, hydroiodic, nitric, carbonic, sulfuric, and phosphoric acid. Appropriate organic acids can be selected from aliphatic, cycloaliphatic, aromatic, arylaliphatic, and heterocyclyl containing carboxylic acids and sulfonic acids, for example formic, acetic, propionic, succinic, glycolic, gluconic, lactic, malic, tartaric, citric, ascorbic, glucuronic, maleic, fumaric, pyruvic, aspartic, glutamic, benzoic, anthranilic, mesylic, stearic, salicylic, p-hydroxybenzoic, phenylacetic, mandelic, embonic (pamoic), methanesulfonic, ethanesulfonic, benzenesulfonic, pantothenic, toluenesulfonic, 2-hydroxyethanesulfonic, sulfanilic, cyclohexylaminosulfonic, algenic, hydroxybutyric, galactaric and galacturonic acid.

The term "patient" and "subject are interchangeable and may be taken to mean any living organism which may be treated with compounds of the present invention. As such, the terms "patient" and "subject" may include, but is not limited to, any non-human mammal, primate or human. In some embodiments, the "patient" or "subject is a mammal, such as mice, rats, other rodents, rabbits, dogs, cats, swine, cattle, sheep, horses, primates, or humans. In some embodiments, the patient or subject is an adult, child or infant. In some embodiments, the patient or subject is a human.

The term "treating" is used herein, for instance, in reference to methods of treating a skin disorder or a systemic condition, and generally includes the administration of a compound or composition which reduces the frequency of, or delays the onset of, symptoms of a medical condition or enhance the texture, appearance, color, sensation, or hydration of the intended tissue treatment area of the tissue surface in a subject relative to a subject not receiving the compound or composition. This can include reversing, reducing, or arresting the symptoms, clinical signs, and underlying pathology of a condition in a manner to improve or stabilize a subject's condition.

By hereby reserving the right to proviso out or exclude any individual members of any such group, including any sub-ranges or combinations of sub-ranges within the group, that can be claimed according to a range or in any similar manner, less than the full measure of this disclosure can be claimed for any reason. Further, by hereby reserving the right to proviso out or exclude any individual substituents, analogs, compounds, ligands, structures, or groups thereof, or any members of a claimed group, less than the full measure of this disclosure can be claimed for any reason. Throughout this disclosure, various patents, patent applications and publications are referenced. The disclosures of these patents, patent applications and publications in their entireties are incorporated into this disclosure by reference in order to more fully describe the state of the art as known to those skilled therein as of the date of this disclosure. This disclosure will govern in the instance that there is any inconsistency between the patents, patent applications and publications cited and this disclosure.

For convenience, certain terms employed in the specification, examples and claims are collected here. Unless defined otherwise, all technical and scientific terms used in this disclosure have the same meanings as commonly understood by one of ordinary skill in the art to which this disclosure belongs.

Various embodiments are directed methods for lightening or whitening skin by topically administering a composition containing cannabinoids to skin. Other embodiments include topical compositions containing cannabinoids for lightening or whitening skin. In some embodiments, the formulations may act as anti-aging formulations that produce a reduction in fine lines and wrinkles, while firming and lifting of the skin following treatment. In some embodiments, the compositions of the invention may promote collagen generation.

The cannabinoids of such embodiments include any of a broad class of compounds that are known to interact with cannabinoid receptors, and encompass endocannabinoids (produced naturally in the body by animals), the phytocannabinoids (found in cannabis and some other plants), and synthetic cannabinoids (manufactured artificially). Example cannabinoids include, but are not limited to, tetrahydropyran analogs, such as, 19-tetrahydrocannabinol, 18-tetrahydrocannabinol, 6,6,9-trimethyl-3-pentyl-6H-dibenzo[b,d]pyran-1-ol, 3-(1,1-dimethylheptyl)-6,6a7,8,10,10a hexahydro-1-1hydroxy-6,6-dimethyl-9H-dibenzo[b,d]pyran-9-ol, (−)-(3S,4S)-7-hydroxy-delta-6 tetrahydrocannabinol-1, 1-dimethylheptyl, (+)-(3S,4S)-7-hydroxy-A-6-tetrahydrocannabinol, and A8-tetrahydrocannabinol-11-oic acid, piperidine analogs, such as, ( )-(6S,6R,9R,10aR) 5,6, 6,7,8,9,10,10a-octahydro-6-methyl-1-3-[(R)-1-methyl-4-phenylbutoxy)-1,9 phenanthridinediol 1-acetate), aminoalkylindole analogs, such as, (R)-(+)-[2,3-dihydro-5-methyl-3 (4-morpholinylm-ethyl)-pyrrolo[1,2,3,-de]-1,4-benzoxazin-6-yl)-1-naphthelenyl-methanone, open pyran-ring analogs, such as, 2-[3-methyl-6-(1-methylethenyl-2-cyclohexen-1-yl]-5-pentyl-1,3 benzendi-ol, and 4-(1,1-dimethylheptyl)-2, 3'-dihydroxy-6'-a-(3-hydroxypropyl)-1',-2',3',4',5',6' hexahydrobiphenyl, lipophilic alkylamides, such as, dodeca-2E, 4E,8Z,10E/Z-tetraenoic-acid isobutylamide, cannabinoid mimetics, salts, solvates, metabolites, and metabolic precursors of these compounds and combinations thereof. In some embodiments, the cannabinoids may be derived plants including hemp, Echinacea purpurea, Echinacea angustifolia, Acmella oleracea, Helichrysum umbraculigerum, Radula marginata, and combinations thereof and oils made from these plants, and in other embodiments, the cannabinoids may be manufactured or chemically synthesized.

The compositions of various embodiments can include any number of cannabinoids in various concentrations; however, in certain embodiments, the cannabinoid may be cannabidiol (2-(6-isopropenyl-3-methyl-5-cyclohexen-1-yl)-5-pentyl-1,3-benzenediol). Cannabidiol has 7 double bonds and 30 stereoisomers. Embodiments include compositions containing each stereoisomer individually and compositions containing a combination of these stereoisomers. In particular embodiments, the compositions used in the methods of embodiments and the compositions of embodiments may include high concentrations of cannabidiol. For example, in some embodiments, cannabidiol may be about 30 w/v % to about 100 w/v % of the cannabinoids in the composition, and in other embodiments cannabidiol may be about 50 w/v % to about 100 w/v %, about 75 w/v % to about 100 w/v %, about 80 w/v % to about 100 w/v %, about 90 w/v % to about 100 w/v % of the cannabinoids in the composition.

Cannabidiol can be obtained by cold-pressing industrial hemp with trace amounts of THC. Cannabidiol in this present invention is provided as a natural constituent of hemp oil.

In some embodiments, the cannabinoids in the composition may be cannabidiol analogs. The term "cannabidiol analogs" refers to synthetically produced compounds that are structurally similar, but not structurally identical, to cannabidiol. Various cannabidiol analogs are known in the art and embodiments encompass such cannabidiol analogs. For example, PCT Publication WO2017/132526 and U.S. Pat. No. 6,630,507, which are each hereby incorporated by reference in their entireties, describes various analogs of cannabidiol. In some embodiments, the analogs of cannabidiol may be of general Formula I:

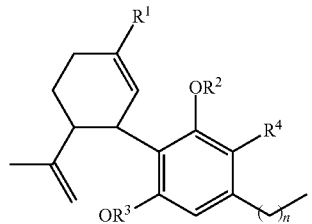

where $R^1$ is hydrogen, methyl, linear or branched $C_2$-$C_{10}$ alkyl, linear or branched $C_2$-$C_{10}$ alkenyl, linear or branched $C_2$-$C_{10}$ substituted alkyl, linear or branched $C_2$-$C_{10}$ substituted alkenyl, $R^2$ and $R^3$ are each, individually, hydrogen, methyl, linear or branched $C_2$-$C_{10}$ alkyl, linear or branched $C_2$-$C_{10}$ substituted alkyl, linear or branched $C_2$-$C_{10}$ alkenyl, linear or branched $C_2$-$C_{10}$ substituted alkenyl, linear or branched $C_2$-$C_{10}$ acyl, linear or branched $C_2$-$C_{10}$ substituted acyl, an amine or amino acid, amino acid ester, $R^4$ is hydrogen, substituted or unsubstituted alkyl, carboxyl, alkoxy, aryl, aryloxy, arylalkyl, halo or amino, and n may an integer of 2 to 10 and the like and salts and solvates thereof. In some embodiments, $R^2$ and $R^3$ may, independently, be a linear or branched, substituted or unsubstituted $C_2$-$C_{10}$ acyl having a carboxylic acid terminus thereby producing a dicarboxylic acid, and salts thereof. Like cannabidiol, cannabidiol analogs can have various isomers. Embodiments include all isomers of the such cannabidiol analogs.

In some embodiments, cannabidiol analogs, such as those described above may be combined with cannabidiol, to produce a mixture of cannabidiol and cannabidiol analogs. Thus, as used herein the term "cannabidiol" encompasses cannabidiol, cannabidiol analogs, and the various isomers of cannabidiol and cannabidiol analogs.

The compositions of embodiments of the invention can include 100% cannabidiol, and oils, solvents, and emulsions containing cannabidiol. For example, in some embodiments, the compositions of the invention may include cannabidiol derived from hempseed oil. Hempseed oil is generally manufactured from varieties of Cannabis sativa that do not contain significant amounts of tetrahydrocannabinol (THC), the psychoactive element of the cannabis plant. This manufacturing process typically includes cleaning the seed to 99.99% before pressing the oil. Hempseed oil generally also contains omega-6 and omega-3 fatty acids. For example, about 30 35% of the weight of hempseed oil are essential fatty acids (EFAs), i.e., linoleic acid, omega-6 (LA, 55%), a-linolenic acid, omega-3 (ALA, 22%), y-linolenic acid, omega-6 (GLA, 1-4%), stearidonic acid, and omega-3 (SDA, 0-2%). Thus, the compositions of some embodiments may contain fatty acids such as omega-6 and omega-3 fatty acids.

The form of the topical formulations of the invention is not limited. Non-limiting examples of the form include an oil, lotion, a cream, a salve, a liniment, an ointment, a gel, a paste, a soap, a shampoo, and a lip balm.

Oils include cannabidiol oil and various plant derived oils containing cannabidiol, such as, hempseed oil, Echinacea purpurea, Echinacea angustifolia, Acmella oleracea, Helichrysum umbraculigerum, Radula marginata, and the like. In some embodiments, cannabidiol isolated from such plants or made synthetically may be formulated with an oil such as, for example, cottonseed oil, olive oil, grapeseed oil, tea tree oil, almond oil, avocado oil, sesame oil, evening primrose oil, sunflower oil, kukui nut oil, jojoba oil, walnut oil, peanut oil, pecan oil, macadamia nut oil, coconut oil, and the like and combinations thereof.

The oils of such embodiments may be supplemented with any of the additives discussed below, or such oils can be incorporated into the creams, lotions, salves, liniments, ointments, gels, pastes, tonics, unguents, soaps, shampoos, and lip balms discussed below. The preparation of a topical compositions that contain dispersed active ingredients is well understood in the art. Typically, such compositions can be prepared as sterile compositions either as liquid solutions or suspensions, aqueous or non-aqueous, however, suspensions in liquid prior to use can also be prepared. The concentration of the cannabinoid or, in certain embodiments, cannabidiol or cannabidiol analogs, in compositions can range from about 0.0002% to about 100% by weight with the balance of the composition being carriers, excipients, diluents, additives, supplements, such as, vitamin E, and the like and combinations thereof.

As used herein, the terms "pharmaceutically acceptable", "physiologically tolerable" and grammatical variations thereof, as they refer to compositions, carriers, excipients, diluents, and reagents represent that the materials are capable of administering upon a mammal without the production of undesirable physiological effects.

The cannabinoid or, in certain embodiments, cannabidiol or cannabidiol analogs, can be mixed with excipients that are pharmaceutically acceptable and compatible with the active ingredient and in amounts suitable for use in the therapeutic methods described herein. For example, the cannabinoid or, in certain embodiments, cannabidiol or cannabidiol analogs, can be dissolved in excipients such as aqueous or saline based solutions or alcohol-based solutions, containing, for example, dextrose, glycerol, and the like and combinations thereof. In some embodiments, the composition can further contain auxiliary substances that enhance the effectiveness of the active ingredient such as wetting or emulsifying agents, pH buffering agents, and the like. These compositions can be administered directly or the compositions can be used as constituent of therapeutic or cosmetic formulation, such as an emulsion, lotion, spray, ointment, cream, foam, mask, soap, and the like. The cannabinoid or, in certain embodiments, cannabidiol or cannabidiol analogs, compositions can make up to about 80% of the therapeutic or cosmetic formulations, and in some embodiments, the cannabinoid or, in certain embodiments, cannabidiol or cannabidiol analogs, can make up about 0.01% to about 75%, about 0.1% to about 50%, about 0.5% to about 25%, or any range or individual concentration encompassed by these ranges. For example, an eye cream can contain about 0.1% to about 10% cannabinoid or, in certain embodiments, cannabidiol or cannabidiol analogs, in a carrier or excipient, and a facial cream can contain about 0.01% to about 20% of cannabinoid or, in certain embodiments, cannabidiol or cannabidiol analogs, in a carrier or excipient. In further embodiments, the cannabinoid or, in certain embodiments, cannabidiol or cannabidiol analogs, in topical formulations can make up about 10 ug/ml to about 10 mg/ml, or about 1 ug/ml to about 10 mg/ml, about 0.1 ug/ml to about 8 mg/ml, about 1 mg/ml to about 5 mg/ml, or any range or individual concentration encompassed by these ranges.

A topical composition of invention can include pharmaceutically acceptable salts of the cannabinoid or, in certain embodiments, cannabidiol or cannabidiol analogs. Pharmaceutically acceptable salts include the acid addition salts that are formed with inorganic acids such as, for example, hydrochloric or phosphoric acids, or such organic acids as acetic, tartaric, mandelic and the like. Salts derived from inorganic bases include, for example, sodium, potassium, ammonium, calcium or ferric hydroxides, and such organic bases as isopropylamine, trimethylamine, ethylamino ethanol, histidine, procaine, and the like.

Physiologically tolerable carriers and excipients are well known in the art. Examples of liquid carriers include sterile aqueous solutions that contain no materials in addition to the active ingredients and water, or water and a buffer such as, for example, sodium phosphate at physiological pH value, physiological saline, such as phosphate-buffered saline and Tris-HCl buffer, and the like and combinations thereof. Aqueous solutions can contain more than one buffer salt, as well as salts such as sodium and potassium chlorides, dextrose, propylene glycol, polyethylene glycol and other solutes.

The compositions of cannabinoid or, in certain embodiments, cannabidiol or cannabidiol analogs, can be formulated into gels, creams, lotions, or ointments. Gels are semi-solid dispersion of liquid or oil particles in a semi-solid medium and may include, for example, petroleum jelly and coco butter. In these mixtures, the cannabinoid, cannabidiol, or cannabidiol analogs may be in the form of a suspension or form a gel with the excipient and can be mixed with solids such as starches and methyl cellulose. Creams refer to semi-solid emulsions of oil and water in approximately equal proportions. They are divided into two types: oil-in-water (O/W) creams, composed of small droplets of oil dispersed in a continuous phase; and water-in-oil (W/O) creams, composed of small droplets of water dispersed in a continuous oily phase. Creams can provide a barrier to protect the skin. Lotions are low- to medium-viscosity topical preparation. Most lotions are oil-in-water emulsions containing an emulsifier such as cetyl alcohol to prevent separation of these two phases, and include, for example, fragrances, glycerol, petroleum jelly, dyes, preservatives, proteins, and stabilizing agents. Ointments are compositions in which oil and water are provided in a ratio of from 7:1 to 2:1, from 5:1 to 3:1, or 4:1. Ointments are generally formulated using oils, waxes, water, alcohols, petroleum products, water, and other agents to prepare formulations with various viscosities and solvent properties. Commonly used ointment formulations include oleaginous base (White Ointment), absorption base, W/O emulsion base (Cold Cream type base), O/W emulsion base (Hydrophilic Ointment), water soluble base, in addition to others. These preparations are used to dissolve or suspend substances or products with medicinal or cosmetic value.

Liquid compositions can also contain liquid phases in addition to and to the exclusion of water. Exemplary of such additional liquid phases are glycerin, vegetable oils such as cottonseed oil, olive oil, grapeseed oil, tea tree oil, almond oil, avocado oil, sesame oil, evening primrose oil, sunflower oil, kukui nut oil, jojoba oil, walnut oil, peanut oil, pecan oil, macadamia nut oil, coconut oil, and the like and combinations thereof, organic esters such as ethyl oleate, and water-oil emulsions.

In certain embodiments, formulations containing cannabinoid, cannabidiol, or cannabidiol analogs compositions of the invention can contain chemical preservatives, such as cetylpyridinium chloride, K-Sorbate, Na-Benzoate, various parabens, other chemical preservatives, and combinations thereof. Other suitable additives include sodium compounds and copper-based compounds. In particular, sodium has been linked to stimulate elastogenesis.

Cosmetic formulations including lotions, creams, soaps, shampoos, lip balms may be designed for moisturizing, anti-aging, or anti-wrinkle, or treating acne, rough skin, dandruff, eczema, and the like as well as lightening or whitening skin.

In some embodiments, topical formulations may further include hydrocortisone or any steroid within Groups I to VII in the US classification system. Group I steroids include, but are not limited to, clobetasol propionate, betamethasone dipropionate, halobetasol, and diflorasone diacetate. Group II steroids include, but are not limited to, fluocinonide, halcinonide, amcinonide, and desoximetasone. Group III steroids include, but are not limited to, triamcinolone acetonide, mometasone furoate, fluticasone propionate, betamethasone dipropionate, and halometasone. Group IV steroids include, but are not limited to, fluocinolone acetonide, hydrocortisone valerate, hydrocortisone butyrate, flurandrenolide, triamcinolone acetonide, and mometasone furoate. Group V steroids include, but are not limited to, fluticasone propionate, desonide, fluocinolone acetonide, and hydrocortisone valerate. Group VI steroids include, but are not limited to, alclometasone dipropionate, triamcinolone acetonide, fluocinolone acetonide, and desonide. Group VII steroids include, but are not limited to, hydrocortisone (2.5%) and hydrocortisone (1%). The amount of hydrocortisone or steroid within Groups I to VII in the topical formulation is not particularly limited, so long as it is a therapeutically effective amount. An amount may be from about 0.01% to about 5%, relative to the total amount of the topical formulation, or about 0.1% to about 1%, relative to the total amount of the topical formulation.

In some embodiments, topical formulations may further include an antibiotic compound. The antibiotic compound is not particularly limited, and may be at least one member selected from the group consisting of ampicillin, bacampicillin, carbenicillin indanyl, mezlocillin, piperacillin, ticarcillin, amoxicillin-clavulanic acid, ampicillin-sulbactam, benzylpenicillin, cloxacillin, dicloxacillin, methicillin, oxacillin, penicillin G, penicillin V, piperacillin tazobactam, ticarcillin clavulanic acid, nafcillin, procaine penicillin, cefadroxil, cefazolin, cephalexin, cephalothin, cephapirin, cephradine, cefaclor, cefamandol, cefonicid, cefotetan, cefoxitin, cefprozil, ceftmetazole, cefuroxime, loracarbef cefdinir, ceftibuten, cefoperazone, cefixime, cefotaxime, cefpodoxime proxetil, ceftazidime, ceftizoxime, ceftriaxone, cefepime, azithromycin, clarithromycin, clindamycin, dirithromycin, erythromycin, lincomycin, troleandomycin, cinoxacin, ciprofloxacin, enoxacin, gatifloxacin, grepafloxacin, levofloxacin, lomefloxacin, moxifloxacin, nalidixic acid, norfloxacin, ofloxacin, sparfloxacin, trovafloxacin, oxolinic acid, gemifloxacin, perfloxacin, imipenem-cilastatin, meropenem, and aztreonam. The amount of the antibiotic compound in the topical formulation is not particularly limited, so long as it is a therapeutically effective amount. An amount is from about 0.01% to about 5%, relative to the total amount of the topical formulation, more preferably from about 0.1% to about 1%, relative to the total amount of the topical formulation.

In some embodiments, topical formulations may further include an antiseptic compound. The antiseptic compound is not particularly limited, and may be at least one member selected from the group consisting of iodine, manuka honey, octenidine dihydrochloride, phenol, polyhexanide, sodium chloride, sodium hypochlorite, calcium hypochlorite, sodium bicarbonate, methyl paraben, and sodium dehydroacetate. The amount of the antiseptic compound in the topical formulation is not particularly limited, so long as it is a therapeutically effective amount. An amount may be from 0.01% to 5%, relative to the total amount of the topical formulation, more preferably from 0.1% to 1%, relative to the total amount of the topical formulation.

In some embodiments, topical formulations may further include an antifungal agent. The antifungal agent is not particularly limited, and may be at least one member selected from the group consisting of amphotericin B, candicidin, filipin, hamycin, natamycin, nystatin, rimocidin, bifonazole, butoconazole, clotrimazole, econazole, fenticonazole, isoconazole, ketoconazole, luliconazole, miconazole, omoconazole, oxiconazole, sertaconazole, sulconazole, tioconazole, albaconazole, fluconazole, isavuconazole, itraconazole, posaconazole, ravuconazole, terconazole, voriconazole, abafungin, amorolfin, butenafine, naftifine, terbinafine, anidulafungin, caspofungin, micafungin, benzoic acid, ciclopirox, flucytosine, griseofulvin, haloprogin, tolnaftate, undecylenic acid, crystal violet, and balsam of Peru. The amount of the antifungal agent in the topical formulation is not particularly limited, so long as it is a therapeutically effective amount. An amount may be from about 0.01% to about 5%, relative to the total amount of the topical formulation, more preferably from about 0.1% to about 1%, relative to the total amount of the topical formulation.

In some embodiments, the topical formulation may further include an anti-acne compound. The anti-acne agent is not particularly limited, and may be at least one member selected from the group consisting of salicylic acid and benzoyl peroxide. The amount of the anti-acne compound in the topical formulation is not particularly limited, so long as it is a therapeutically effective amount. An amount of from about 0.01% to about 5%, relative to the total amount of the topical formulation, or about 0.1% to about 1%, relative to the total amount of the topical formulation.

In some embodiments, topical formulations may include a humectant, which can be referred to as a soothing, smoothing, moisturizing or protective agent. The humectant is not particularly limited, and may be at least one member selected from the group consisting of calamine, dodecylsulphate, sodium lauryl sulphate (SLS), a polyoxyethylene ester of polysorbitan, such as monooleate, monolaurate, monopalmitate, monostearate esters, esters of sorbitan, the polyoxyethylenes ethers, the sodium dioctylsulphosuccinate (DOSS), lecithin, and sodium docusate. Sodium lauryl sulphate and calamine are the most preferred humectants. The amount of the humectant in the topical formulation is not particularly limited, so long as it is a therapeutically effective amount. An amount may be from about 0.01% to about 5%, relative to the total amount of the topical formulation, more preferably about 0.1% to about 1%, relative to the total amount of the topical formulation.

In some embodiments, topical formulations may contain a UV-absorbing compound, which can be referred to as a sunscreen agent. The UV-absorbing compound is not particularly limited, and may be at least one member selected from the group consisting of glyceryl PABA, padimate 0, roxadimate, dioxybenzone, oxybenzone, sulisonbenzone, octocrylene, octyl methoxycinnamate, ethoxyethyl p-methoxycinnamate, homomenthyl salicylate, ethylhexyl salicylate, trolamine salicylate, avobenzone, ecamsule, ensulizole, bemotrizinol, and bisoctrizole. The amount of the UV-absorbing compound in the topical formulation is not particularly limited, so long as it is a therapeutically effective amount. An amount may be from about 0.01% to about 5%, relative to the total amount of the topical formulation or about 0.1% to about 1%, relative to the total amount of the topical formulation.

In some embodiments, topical formulations may include an analgesic agent. The analgesic agent is not particularly limited, and is preferably at least one member selected from the group consisting of methyl salicylate, codeine, morphine, methadone, pethidine, buprenorphine, hydromorphine, levorphanol, oxycodone, fentanyl, and a non-steroidal anti-inflammatory drug (NSAID). The amount of the analgesic agent in the topical formulation is not particularly limited, so long as it is a therapeutically effective amount. An amount may be from about 0.01% to about 5%, relative to the total amount of the topical formulation, or about 0.1% to about 1%, relative to the total amount of the topical formulation.

An "effective amount" is a predetermined amount of cannabinoid, cannabidiol, or cannabidiol analogs calculated to achieve the desired effect, for example, to effectively promote lighten the color of skin, reduce production of melanin, diminish the amount of melanin in skin, reduce visible redness, or combinations thereof. Thus, the dosage ranges for the administering of cannabinoid, cannabidiol, or cannabidiol analogs are those large enough to produce the desired effect without causing adverse side effects. Generally, the dosage will vary with the age, condition, and sex of the patient, and can be determined by one of skill in the art. The dosage can be adjusted in the event of any complication.

The compositions and formulations discussed above, can be administered in a manner compatible with the dosage formulation, and in a therapeutically effective amount. Suitable regimes for administration are also variable, but are typified by an initial administration followed by repeated doses at one or more time intervals by a subsequent administration. Where a single composition is not available for a treatment, or where such a composition is not desirable, administration of composition may also include the application of several different compositions sequentially to achieve a desired effect.

"Providing" when used in conjunction with a therapeutic means to administer a therapeutic directly onto a target tissue or to administer a therapeutic to a patient whereby the therapeutic positively impacts the tissue to which it is targeted. Thus, as used herein, the term "providing", when used in conjunction with cannabinoid or, in certain embodiments, cannabidiol or cannabidiol analogs, can include, but is not limited to, providing a cannabinoid or, in certain embodiments, cannabidiol or cannabidiol analogs, onto the target tissue. "Providing" a composition may be accomplished by topical administration, or by either method in combination with other known techniques. Such combination techniques include heating, radiation and ultrasound.

Heating skin on a patient may open pores, activate the various mechanisms of a cell, and increase diffusion into said tissue and cells. Thus, heating in connection with providing a therapeutic composition is an aspect of the invention.

Embodiments can further include local administration of compositions or formulations containing cannabinoid, cannabidiol, or cannabidiol analogs to skin of a mammal. Local administration is typically carried out by topical administration of a liquid, gel, cream, ointment, or lotion containing the compositions of various embodiments.

In some embodiments, the formulations can be in the form of a soap, which are formulations that comprise a salt of a fatty acid. Soaps are mainly used as surfactants for washing, bathing, and cleaning, but they are also used in textile spinning and are important components of lubricants. Soaps for cleansing are usually obtained by treating vegetable or animal oils and fats with a strongly alkaline solution. Fats and oils are composed of triglycerides; three molecules of fatty acids are attached to a single molecule of glycerol. The alkaline solution, which is often called lye (although the term "ye soap" refers almost exclusively to soaps made with sodium hydroxide), is believed to promote a chemical reaction known as saponification. In saponification, the fats are first hydrolyzed into free fatty acids, which then combine with the alkali to form crude soap. Glycerol (glycerine) is usually liberated and is either left in or washed out and recovered as a useful byproduct, depending on the process employed.

In some embodiments, the topical formulations can be in the form of a shampoo, which is a hair care product used for the removal of oils, dirt, skin particles, dandruff, environmental pollutants, and other contaminant particles that gradually build up in hair.

Additional embodiments are directed to methods for making the topical formulations including cannabinoid or, in certain embodiments, cannabidiol or cannabidiol analogs. Such methods may include dispersing the cannabinoid, cannabidiol, or cannabidiol analogs into mineral oil or silicone oil to obtain an oil phase; dispersing an emulsifier, a thickener; and a stabilizer into water in a separate vessel to obtain an aqueous phase; and blending the oil phase and the aqueous phase to form an emulsion. In various embodiments, such methods may include dispersing cannabinoid, cannabidiol, or cannabidiol analogs into the aqueous phase or the emulsion, rather than into the oil phase. In some embodiments, the method further include the step of heating during at the steps of obtaining an oil phase or dispersing an emulsifier, a thickener; and a stabilizer into water in a separate vessel to obtain an aqueous phase. Temperatures of this heating are not particularly limited, so long as the oil phase and the aqueous phase result from the dispersing.

In some embodiments, methods for making the topical formulations can include mixing an oil phase including cannabinoid, cannabidiol, or cannabidiol analogs and an emulsifier with an aqueous phase to form a mixture, and heating said mixture at a temperature of from 45° C. and 85° C. to form an aqueous emulsion. Emulsifiers include, but are not limited to, cetyl alcohol, stearic acid, and a mixture thereof. The water phase may further include a stabilizing agent such as VEEGUM® or CARBOPOL®, and further embodiments, include adding one or more additives, such as fragrances, glycerol, petroleum jelly, colorants, dyes, preservatives, proteins, and the like. Such methods may produce lotions.

In further embodiments, methods for making the topical formulation can include combining a surfactant such as, for example, sodium lauryl sulfate, sodium laureth sulfate, or combinations thereof with a co-surfactant such as cocamidopropyl betaine, in an aqueous phase and mixing the aqueous phase with an oil phase containing cannabinoid, cannabidiol, or cannabidiol analogs to form a viscous liquid. Methods can include adding other additives, such as salt (sodium chloride), a preservative, and fragrance, to the aqueous phase.

Further embodiments are directed to methods for whitening or lightening skin of a subject and/or reducing fine lines and wrinkles, firming and lifting of the skin, promoting collagen production, generally reducing the signs of aging, and combinations thereof that include applying an effective amount of a topical formulation containing cannabinoid, cannabidiol, or cannabidiol analogs such as those describe above according to skin of a subject. Non-limiting examples of targeted dermatological diseases include eczema, psoriasis, sunburn, contact dermatitis, poison ivy and conditions caused by other plant materials containing urushiol or related molecules, type 1 and type 2 herpes, insect bites, anal itching, vaginal itching, acne, warts and other acute and chronic dermatoses afflicting humans, and use as a topical analgesic for muscle and arthritic pain. Psoriasis is the preferred targeted dermatological disease.

EXAMPLES

Although the present invention has been described in considerable detail with reference to certain preferred embodiments thereof, other versions are possible. Therefore, the spirit and scope of the appended claims should not be limited to the description and the preferred versions contained within this specification. Various aspects of the present invention will be illustrated with reference to the following non-limiting examples.

Example 1

Weighed 1.5 grams of subcritical $CO_2$ extracted CBDA (40.13 wt. % CBDA) into jar. To this was added 30 grams of Jerkins "Ultra-Healing" dry skin cream as a suitable base. This was thoroughly mixed by hand until a uniform, light yellow cream (1). A second control sample was prepared of only 30 grams Jerkins "Ultra-Healing" dry skin cream (2).

These samples were applied two times daily to left and right hands independently for 35 days. Control cream (2), 0.5 milliliters was applied during the morning and evening every day, thoroughly 1 inch above the wrist of the left hand and evening every day over the entire back of hand to the fingertips. Lightening cream (1), 0.5 milliliters was applied during the morning, thoroughly 1 inch above the wrist of the right hand and over the entire back of hand to the fingertips, and.

Figure 1B:
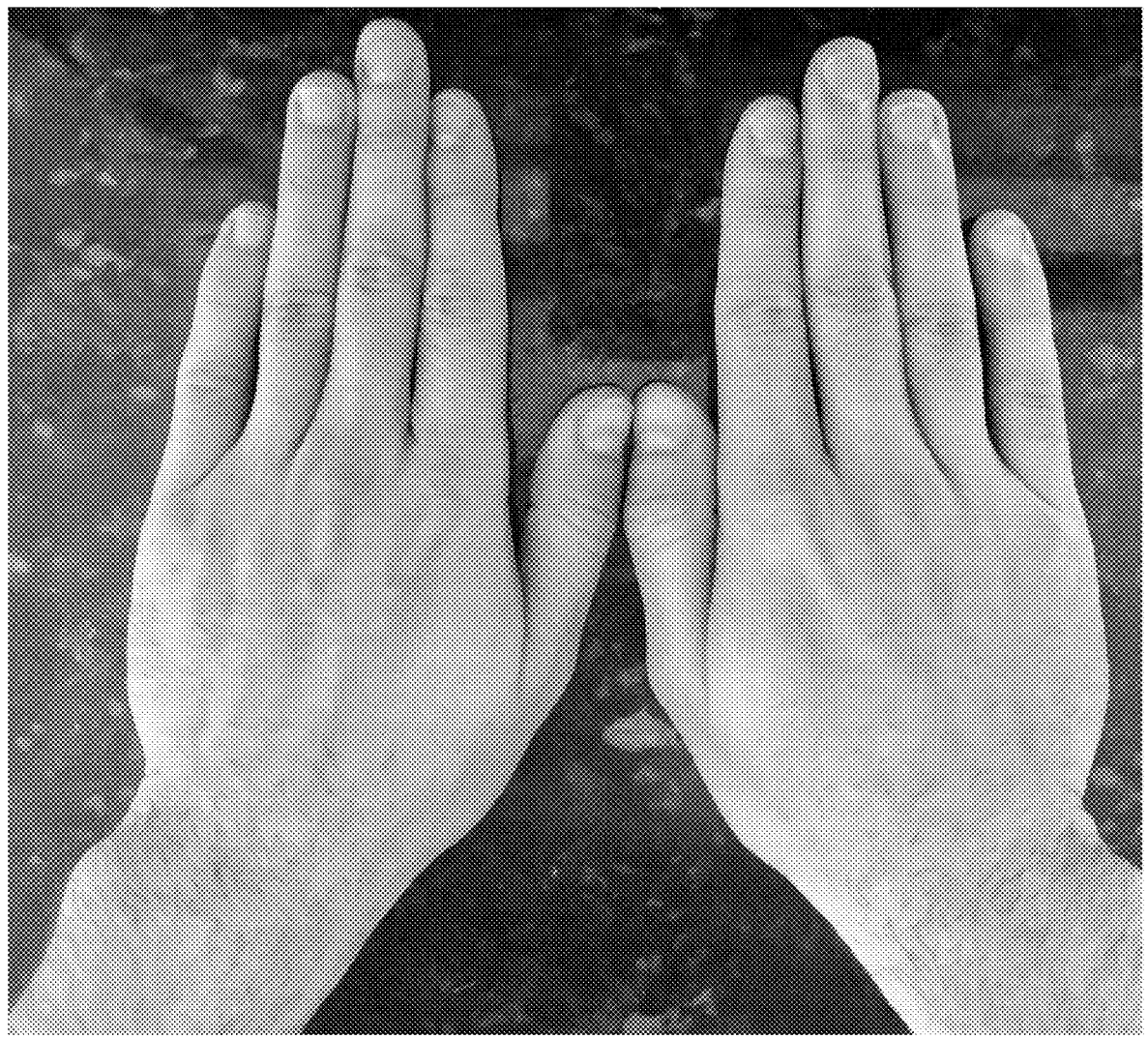
Figure 1C:
Figure 2:
FIG. 2 shows the hand of a subject after treatment with a CBDA skin lightening composition. Skin lightening and reduction in freckles on the back of the hand as compared to the forearm are seen.

Noticeable lightening of the right hand began to occur after 2 weeks (about 14 days) of application, and lightening continued for the duration of experiment. The left hand unchanged throughout the treatment period. See FIG. 1A-C. No irritation, rash, redness, itchiness or discomfort of any kind was reported during this trial.

The invention claimed is:

1. A method for lightening skin tone, comprising topically administering a composition containing about 0.5 wt. % to about 25 wt. % *Cannabis* plant-isolated cannabidiol or cannabidiol analog or based on the total weight of the composition, wherein the isolated cannabidiol or cannabidiol analog is present in an amount of is about 90 w/v % to about 100 w/v % of the total cannabinoids in the composition.

2. The method of claim 1, wherein the lightening comprises lightening color of skin, reducing production of melanin, diminishing the amount of melanin in skin, reducing redness of skin, or combinations thereof.

3. The method of claim 1, wherein the composition comprises about 10 ug/ml to about 10 mg/ml isolated cannabidiol based on the total weight of the composition.

4. The method of claim 1, wherein the composition comprises about 0.1 ug/ml to about 8 mg/ml isolated cannabidiol based on the total weight of the composition.

5. The method of claim 1, wherein the composition is a semi-solid emulsion of oil and water in approximately equal proportions.

6. The method of claim 1, wherein the composition is an oil-in-water (O/W) cream or a water-in-oil (W/O) cream.

7. The method of claim 1, wherein the composition further comprises an agent selected from the group consisting of steroids, antibiotics, antiseptics, antifungals, anti-acne compounds, humectants, UV-absorbing compounds, analgesics, and combinations thereof.

8. A method for reducing signs of aging, comprising topically administering a composition containing about 0.5 wt. % to about 25 wt. % *Cannabis* plant-isolated cannabidiol or cannabidiol analog based on the total weight of the composition, wherein the isolated cannabidiol or cannabidiol analog is present in an amount of is about 90 w/v % to about 100 w/v % of the total cannabinoids in the composition.

9. The method of claim 8, wherein the reducing the signs of aging comprises reducing fine lines, reducing wrinkles, firming skin, lifting skin, and reducing sagging.

10. The method of claim 8, wherein the composition comprises about 0.1 ug/ml to about 8 mg/ml isolated cannabidiol based on the total weight of the composition.

11. The method of claim 8, wherein the composition is a semi-solid emulsion of oil and water in approximately equal proportions.

12. The method of claim 8, wherein the composition is an oil-in-water (O/W) cream or a water-in-oil (W/O) cream.

13. The method of claim 8, wherein the composition further comprises an agent selected from the group consisting of steroids, antibiotics, antiseptics, antifungals, anti-acne compounds, humectants, UV-absorbing compounds, analgesics, and combinations thereof.

14. The method of claim 1, wherein the isolated cannabidiol or cannabidiol analog is selected from the group consisting of compounds of Formula I:

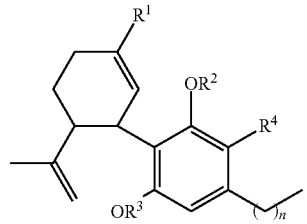

wherein:
$R^1$ is hydrogen, methyl, linear or branched $C_2$-$C_{10}$ alkyl, linear or branched $C_2$-$C_{10}$ alkenyl, linear or branched $C_2$-$C_{10}$ substituted alkyl, linear or branched $C_2$-$C_{10}$ substituted alkenyl;

$R^2$ and $R^3$ are each, individually, hydrogen, methyl, linear or branched $C_2$-$C_{10}$ alkyl, linear or branched $C_2$-$C_{10}$ substituted alkyl, linear or branched $C_2$-$C_{10}$ alkenyl, linear or branched $C_2$-$C_{10}$ substituted alkenyl, linear or branched $C_2$-$C_{10}$ acyl, linear or branched $C_2$-$C_{10}$ substituted acyl, an amine or amino acid, amino acid ester;

$R^4$ is hydrogen, substituted or unsubstituted alkyl, carboxyl, alkoxy, aryl, aryloxy, arylalkyl, halo or amino; and n is an integer of 2 to 10 and salts and solvates thereof.

15. The method of claim 1, wherein lightening comprises reducing production of melanin or diminishing the amount of melanin in skin.

16. The method of claim 8, wherein the isolated cannabidiol or cannabidiol analog is selected from the group consisting of compounds of Formula I:

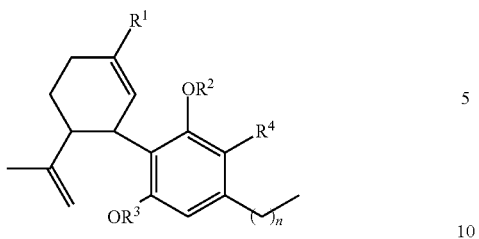

wherein:
$R^1$ is hydrogen, methyl, linear or branched $C_2$-$C_{10}$ alkyl, linear or branched $C_2$-$C_{10}$ alkenyl, linear or branched $C_2$-$C_{10}$ substituted alkyl, linear or branched $C_2$-$C_{10}$ substituted alkenyl;

$R^2$ and $R^3$ are each, individually, hydrogen, methyl, linear or branched $C_2$-$C_{10}$ alkyl, linear or branched $C_2$-$C_{10}$ substituted alkyl, linear or branched $C_2$-$C_{10}$ alkenyl, linear or branched $C_2$-$C_{10}$ substituted alkenyl, linear or branched $C_2$-$C_{10}$ acyl, linear or branched $C_2$-$C_{10}$ substituted acyl, an amine or amino acid, amino acid ester;

$R^4$ is hydrogen, substituted or unsubstituted alkyl, carboxyl, alkoxy, aryl, aryloxy, arylalkyl, halo or amino; and n is an integer of 2 to 10 and salts and solvates thereof.

17. The method of claim 8, wherein wherein the reducing signs of aging comprises reducing production of melanin or diminishing the amount of melanin in skin.

\* \* \* \* \*